United States Patent
Jelinski et al.

[11] Patent Number: 6,120,119
[45] Date of Patent: Sep. 19, 2000

[54] INCUBATOR/DRYING OVEN HAVING HANDLE FOR CHECKING CLOSURE OF DOOR

[75] Inventors: Sonja Jelinski, Hasselroth; Stefan Ferger, Ranstadt; Harald Langen, Babenhausen, all of Germany

[73] Assignee: Kendro Laboratory Products, GmbH, Hanau, Germany

[21] Appl. No.: 09/240,530

[22] Filed: Jan. 29, 1999

[30] Foreign Application Priority Data

Jan. 30, 1998 [DE] Germany .......................... 198 03 601

[51] Int. Cl.⁷ .................................................. A47B 81/00
[52] U.S. Cl. .............................. 312/291; 74/519; 74/523; 74/543; 74/545; 292/DIG. 21
[58] Field of Search .................... 312/215, 222, 312/291, 298, 405; 292/200, 202, 203, 336.3, DIG. 5, DIG. 21, DIG. 30; 74/528, 543, 544, 545

[56] References Cited

U.S. PATENT DOCUMENTS

| | | | |
|---|---|---|---|
| 506,387 | 10/1893 | Bahlsen | 292/202 X |
| 1,382,837 | 6/1921 | Jurek | 312/291 X |
| 4,336,329 | 6/1982 | Hesse et al. | 435/3 |
| 4,706,478 | 11/1987 | Swan et al. | 292/336.3 X |
| 5,519,188 | 5/1996 | Yuichi et al. | 219/407 |

FOREIGN PATENT DOCUMENTS

| | | | |
|---|---|---|---|
| 590165 | 3/1959 | Italy | 312/291 X |
| 280855 | 8/1924 | United Kingdom | 74/528 X |
| 379890 | 8/1924 | United Kingdom | 292/202 X |
| 2196050 | 9/1986 | United Kingdom | 292/202 X |

OTHER PUBLICATIONS

Heraeus, Brutschrank Fur Zellkulturen B 5060 EK/CO2 mit CO2—oder pH–Wert–Regler, Mar. 1977.
Heraeus, Begasungsbrutschranke fur Zellkulturen, Feb. 1989.

Primary Examiner—Anthony D. Barfield
Assistant Examiner—Michael J. Fisher
Attorney, Agent, or Firm—Workman, Nydegger & Seeley

[57] ABSTRACT

An incubator or drying oven is provided having a housing bounding a useful space. The useful space communicates with the exterior through a front opening. An inner door is hingedly mounted to the housing and is configured to selectively cover the front opening. An outer door is also hingedly mounted to the housing and is configured to selectively cover the inner door. Mounted on the housing adjacent to the front opening is a locking element. The locking element has a slot formed on the side thereof. A latching assembly is mounted to the inner door. The latching assembly includes a hub rotatably mounted to the inner door about a first axis, a tongue projecting from the hub and configured to be received within the slot of the locking element, and a handle attached to the hub opposite the tongue. The handle is rotatably connected to the hub about a second axis that is substantailly perpendicular to the first axis. A spring continually biases the handle away from the inner door. The handle is selectively movable relative to the first axis between a first position and a second position. In the first position at least a portion of the handle is disposed over at least a portion of the locking element so that the handle functions as a spacing element that prevents complete closing of the outer door. In the second position the handle is spaced apart from the locking element such that the outer door is free to completely close.

23 Claims, 4 Drawing Sheets

INCUBATOR/DRYING OVEN HAVING HANDLE FOR CHECKING CLOSURE OF DOOR

This application claims priority under 35 U.S.C. §119 to German patent application no. 198 03 601.9, filed Jan. 30, 1998, which is incorporated herein by specific reference.

BACKGROUND OF THE INVENTION

1. The Field of the Invention

The present invention relates to incubators and drying ovens and, more specifically, methods and apparatus for checking the closure of at least one inner door and one outer door of an incubator or drying oven.

2. Present State of the Art

The prior art discloses gassing incubators that bound a useful space. The useful space is configured to receive materials for processing by the gassing incubator. The useful space communicates with the exterior through an opening. The opening is selectively closed by an inside door, which is typically made of a transparent material, and a second outside door. The inside or transparent door in the gassing incubator is used to protect the inside of the useful space from losses of heat, moisture, and gas when the outside door is opened.

Checking whether the inside door is open when the outside door is locked turns out to be a problem. The closure of the inside door requires increased attentiveness or an additional electric control indicator. This entails greater technical expense due to additional components.

OBJECTS AND BRIEF SUMMARY OF THE INVENTION

One object of the present invention to make it possible to check whether the inner door of a drying oven or incubator is securely locked, while trying to use the simplest possible design which does not increase the technical expense.

To achieve the foregoing objective and in accordance with the invention as broadly disclosed herein, a drying oven or incubator is provided having a housing bounding a useful space. The useful space communicates with the exterior through a front opening. The front opening is selectively closed by at least one inner door, preferably made of a transparent material, such as glass, and an outer door.

The inner door has a first side edge and an opposing second side edge. The first side edge is hingedly mounted to the housing adjacent the front opening so that the inner door can pivot about a vertical pivot axis. The outer door is also hingedly mounted to the housing and is configured to overlie the inner door.

A latch assembly is mounted on the second side edge of the inner door and is configured to engage a locking element. The locking element is positioned on the front side area of the housing adjacent to the front opening. The latch assembly includes a foldable handle having a rigid tongue connected thereto. The latch assembly is configured such that rotation of the handle results in corresponding rotation of the rigid tongue.

The handle and corresponding tongue can be rotated between a first and second position. In the first position, the inner door is unlocked and the handle is disposed over a portion of the locking element. In this position, the handle acts as a spacing element or block between the locking element and the outer door, thereby preventing the outer door from locking closed. That is, the handle blocks the closure of the outer door by resting on the locking element. Rotating the handle into the second position results in the tongue engaging the locking element such that the inner door is locked with the housing. In this second position, the handle is rotated out of alignment with the locking element. As such, the handle no longer functions as a spacing element and the outer door can be selectively closed and locked to the housing.

No complicated closing mechanisms and signal outputs are required by the present invention. Accordingly, a substantial advantage can be seen in the simple operation and simplified manufacturing and maintenance.

In a preferred embodiment of the invention and method of use, the locking element has a slit which serves as a catch opening which receives the tongue of the latch assembly. The slit narrows at least partially in the latching direction. As a result, pivoting the tongue into the slit of the locking element causes the tongue, together with the inner door, to press against the housing in the direction of the inside space.

It is also an advantage for the inner door to be pressed against a peripheral sealing element surrounding the opening of the useful space. This enables the useful space to be closed off from the atmosphere. The useful space, however, can still be observed from outside through the inner door, which is preferably made as a glass door.

In addition to the reduced manufacturing and maintenance expense, another advantage of the present invention is that the present invention makes it possible for less proficient operators to insure, in a simple and clear way, that the drying oven or incubator is sealed. Furthermore, the fact that the latching mechanism is located outside the useful space makes it possible to disinfect the latching mechanism simply and safely.

In one embodiment of the incubator or drying oven, the rotatable handle is made as a folding, spring-loaded spacing element which is arranged diametrically opposite the latching tongue. With the outer door open, the gripping surface of the handle and the plane of the inner door are at an angle of approximately 70° to one another. This angle is reduced to between about 0 and about 5° by pressing the outer door against the handle, both when the inner door is open and when it is closed. In one embodiment, another advantage of the present invention is that the outer door cannot exert any force on the rotating mounting of the tongue and handle.

When the tongue is unlatched, the handle acts, at least partly, as a spacing element located between the locking element and the outer door. When the tongue is latched and the outer door is closed, the handle is approximately in the same plane as the outside contour of the locking element.

Here the double function of the handle with the latching tongue as a closing and checking element turns out to be advantageous.

The useful space can be reopened by rotating the handle clockwise. The fact that its security function is purely mechanical makes this locking device for inner doors of drying ovens or gassing incubators especially economical as well as clear and dependable.

In a preferred embodiment, the inner door consists of a transparent material, preferably glass, so that the useful space can advantageously be visually monitored from the outside without atmospheric interference.

Another advantageous embodiment makes it possible to divide the useful space, using at least one horizontal partition having a sealing element on its front side, into two or more sections, each of which can be locked with an inner door. Each inner door has a latching element with a tongue which, when the door is closed, engages in a locking element which corresponds to the respective tongue and which is in the side edge area of the housing.

In such an arrangement, it turns out to be especially advantageous that certain sections of the useful space can be partially loaded, while the other sections of the useful space are protected from losses of heat, moisture, or gas.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENT

Figure 1:
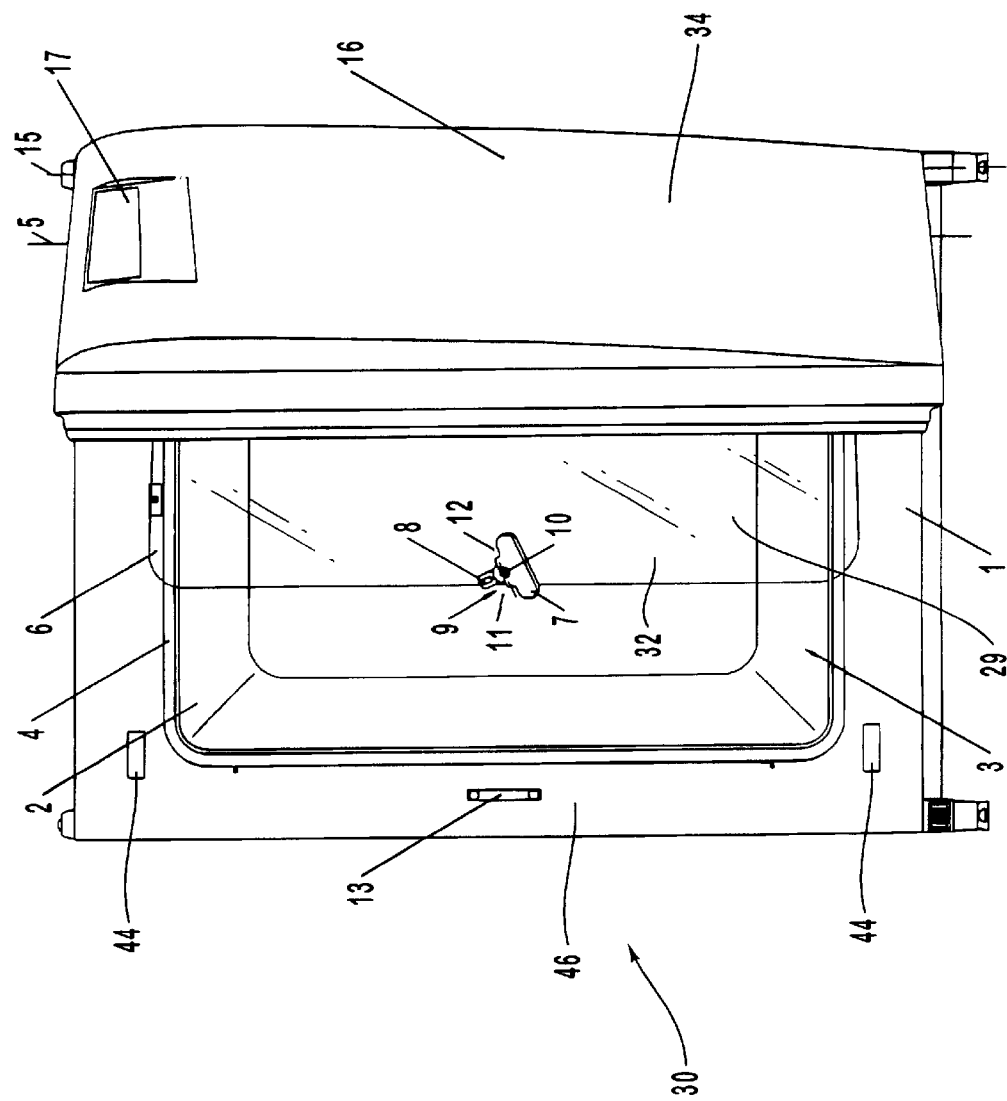
FIG. 1 shows a schematic perspective view of a drying oven or gassing incubator with its inner door open.
Figure 2:
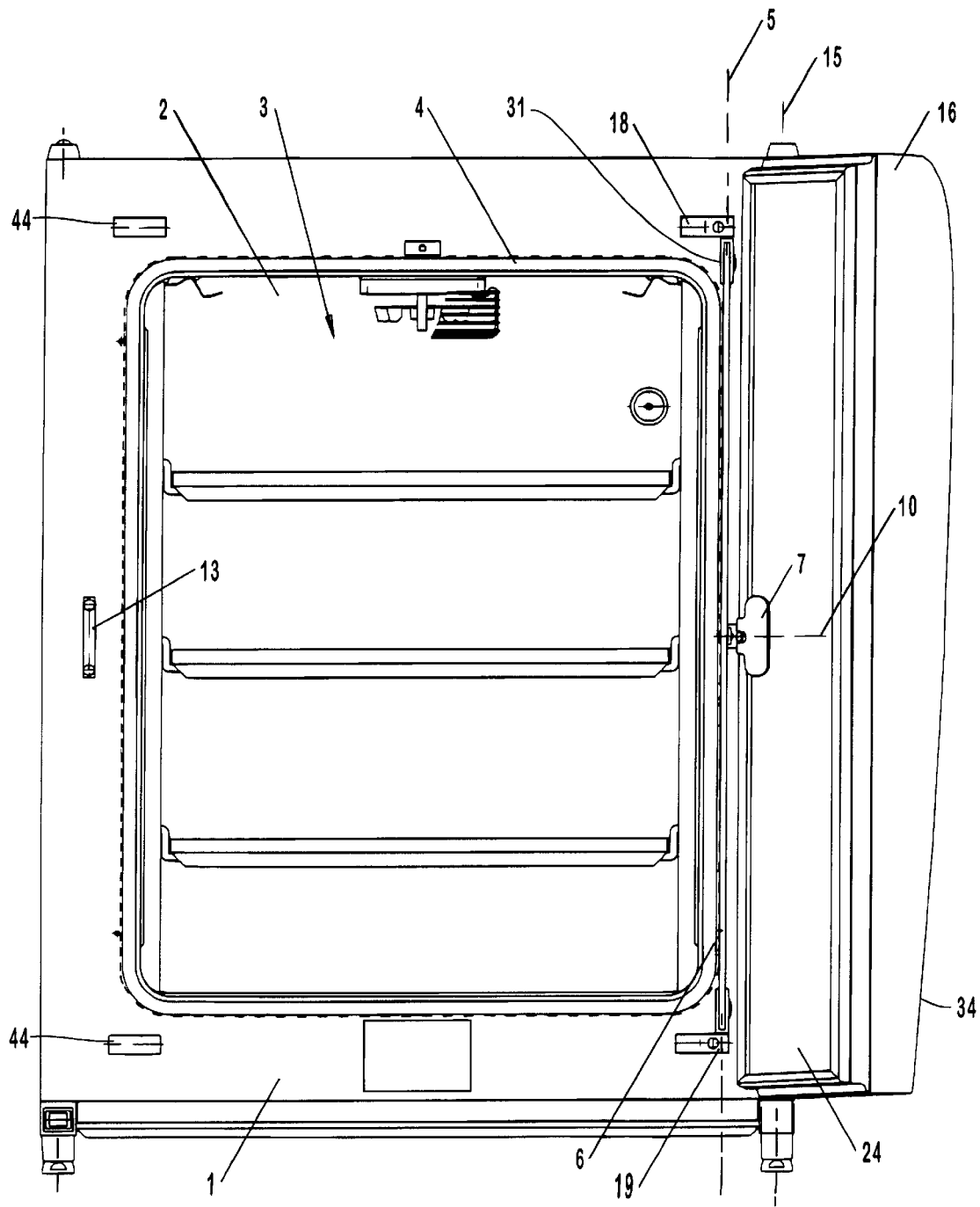
FIG. 2 shows a simplified schematic front view of the opened drying oven or gassing incubator with the rotating handle and locking element, with the control part omitted.

Depicted in FIGS. 1 and 2 is a drying oven or incubator 30 comprising a housing 1 bounding a useful space 2. Useful space 2 communicates with the exterior through a front opening 3. Mounted on housing 1 so as to encircle opening 3 is a peripheral sealing element 4. Opening 3 can be selectively closed and locked by an inner door 6 and an outer door 16. Inner door 6 is preferably made of a transparent material, such as glass. Inner door 6 has a front face 29 that extends between a first side edge 31 and an opposing second side edge 32.

First side edge 31 of inner door 6 is mounted to housing 1 adjacent to opening 3 by hinges 18 and 19. In this configuration, inner door 6 is free to pivot on hinges 18 and 19 about a vertical axis 5. Outer door 16 is also hingedly mounted to housing 1 so as to freely rotate about a pivot axis 15. Outer door 16 has an inside wall 24 and an opposing outside wall 34. Positioned on outside wall 34 is a control part 17 having display and adjustment elements. When outer door 16 is closed, outer door 16 overlies inner door 6 and engages magnetic contacts 44 positioned on housing 1. Engagement between outer door 16 and magnetic contacts 44 completes an electrical circuit which signals that outer door 16 is properly closed.

A latching assembly 9 is mounted in an opening on second side edge 32 of inner door 6 so that latching assembly 9 can rotate about a first axis of rotation 10. Latching assembly 9 is configured to engage a locking element 13. Locking element 13 is positioned on a front side 46 of housing 1 adjacent to opening 3. Latching assembly 9 includes a hub 11 rotatably mounted to inner door 6 so as to project from front face 29 at second side edge 32. Hub 11 is disposed along axis of rotation 10. A rigid tongue 8 radially outwardly projects from hub 11 adjacent to front face 29. In one embodiment, tongue 8 is attached to hub 11 by a form-fit contact.

Disposed at the free end of hub 11 is an elongated handle 7. As depicted in FIG. 3a, handle 7 is mounted to hub 11 by rotatably engaging a pin 36 radially outwardly projecting from the free end of hub 11. Pin 36 enables handle 7 to rotate about a folding or second axis 12 extending through pin 36 without rotation of hub 11. Folding axis 12 is substantially perpendicular to first axis 10. The attachment of handle 7 by pin 36 also permits handle 7 to rotate about first axis 10 to facilitate concurrent rotation of tongue 8.

Handle 7 is configured to rotate about folding axis 12 between an angle of about 3° to about 70° relative to the plane of inner door 6. A coil spring 14 positioned along folding axis 12 continually biases handle 7 into the upstanding or 70° orientation relative to the plane of inner door 6. As a result of the orientation of handle 7 being less than 90°, applying a load against handle 7, such as by closing outer door 16 against inner door 6, causes handle 7 to be folded down toward inner door 6. That is, closing outer door 16 closes the angle of handle 7 from about 70° to about 3°.

Figure 3B:
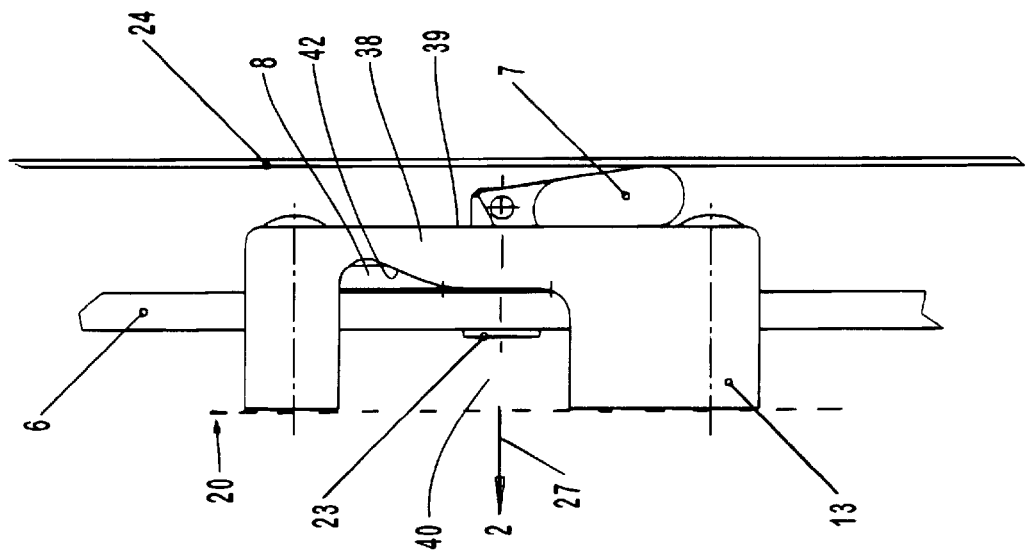
FIGS. 3a and 3b show the action of the handle when the inner door is unlocked, the handle coming to lie on the locking element between the inner and outer door and thus acting as a spacing element with respect to the outer door. Only fragments of the inner door and outer door are shown. The edge area of the housing part provided for fastening the locking element is symbolically suggested in FIG. 3b by a dashed line, which represents part of the surface.
Figure 3A:
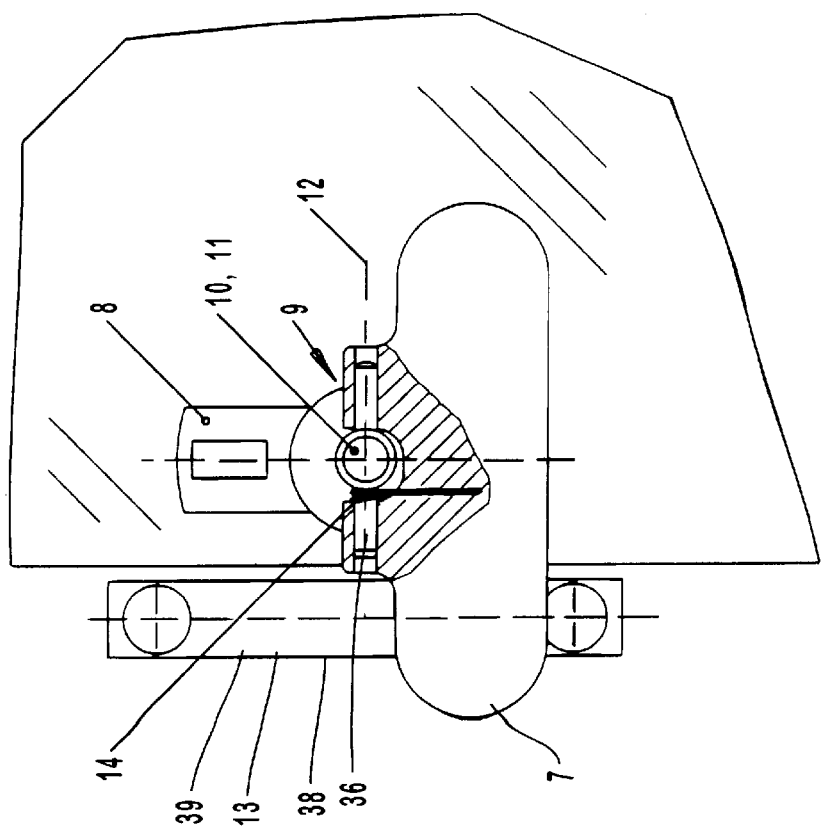

As depicted in FIGS. 3a and 3b, in one embodiment locking element 13 comprises a catch 38 having a top surface 39 and a slot 40 formed in the side thereof. Slot 40 serves as a catch opening which receives tongue 8 of latch assembly 9. Slot 40 is in part bounded by a bearing surface 42. A portion of bearing surface 42 slopes toward housing 1 so that slot 40 narrows.

During use, latch assembly 9, including handle 7 and corresponding tongue 8, can be selectively rotated around first axis 10 between a first position and a second position. In the first position, as shown in FIGS. 3a and 3b, tongue 8 is oriented in a spaced apart substantially parallel alignment with locking element 13 while handle 7 is disposed over top surface 39 of catch 38. In this first position, inner door 6 is unlocked. Attempting to close outer door 16 results in handle 7 being biased between top surface 39 of locking element 13 and inner wall 24 of outer door 16. Handle 7 thus acts as a spacing element which prevents full closure and locking of outer door 16. That is, as a result of handle 7 being biased between catch 38 and inner wall 24 of outer door 16, outer door 16 is blocked or otherwise prevented from fully closing. Thus, outer door 16 cannot engage magnetic contacts 44 to close the circuit. In this way, there is always a load on locking element 13 or folding handle 7, while the bearing along rotational axis 10 of inner door 6 remains unloaded. This ensures that accidental closing outer door 16 does not cause any damage to inner door 6 if it is not latched.

The profile perspective in FIG. 3b also shows inner door 6 and a small part of tongue 8. The surface of housing 1 on which locking element 13 is secured is symbolically shown by a dashed line 20. The end of hub 11 of latching element 9 facing the useful space is marked with the reference number 23.

Figure 4B:
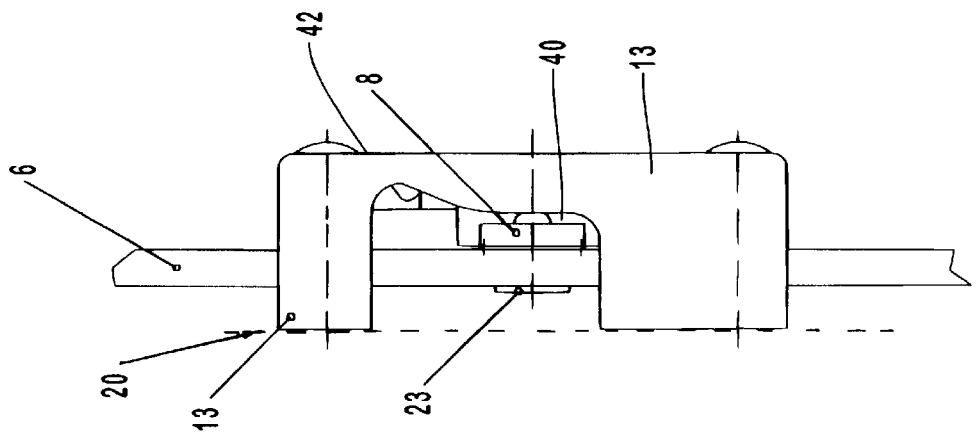
FIGS. 4a and 4b, like FIGS. 3a and 3b, show fragments of a part of the inner door with the handle on it and the locking element in latched position, however with the handle and the locking element lying in the same plane, so that the handle no longer acts as a spacing element.
Figure 4A:
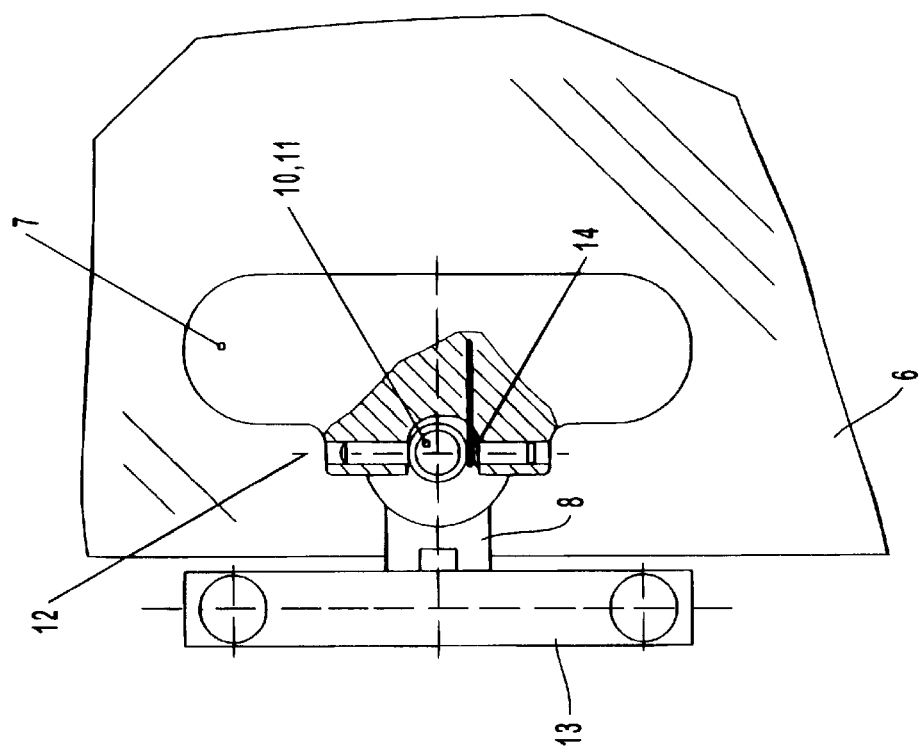

As depicted in FIGS. 4a and 4b, pushing inner door 6 against sealing element 4 (shown in FIG. 1) on housing 1 and rotating handle 7 counter clockwise 90°, positions handle 7 and tongue 8 in the second position. Rotation of tongue 8 into the second position causes tongue 8 to be received within slot 40 of locking element 13, thereby locking inner door 6 closed. As tongue 8 is received within slot 40, tongue 8 rides against bearing surface 42. As a result of bearing surface 42 sloping or angling toward housing 1, pivoting of tongue 8 into slot 40 forces tongue 8 and inner door 6 in the direction of arrow 27, as shown in FIG. 3b. As a result, inner door 6 is pressed against housing 1, more specifically, sealing element 4, thereby sealing opening 3 closed.

In the second position, handle 7 is rotated out of alignment with locking element 13. More specifically, handle 7 is spaced apart from and is in substantial parallel alignment with locking element 13. As such, handle 7 can no longer bias against locking element 13 and thus no longer functions as a spacing element. Outer door 16 is thus free to close and lock. As outer door 16 is closed, handle 7 simply rotates or folds-in around folding axis 12 so that handle 7 lies in approximately the same plane as locking element 13.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An incubator or drying oven comprising:
   (a) a housing bounding a useful space, the useful space communicating with the exterior through a front opening;
   (b) an inner door hingedly mounted to the housing and configured to selectively cover the front opening;
   (c) an outer door hingedly mounted to the housing and configured to selectively cover the inner door;
   (d) a locking element mounted on the housing adjacent to the front opening, the locking element having a slot formed thereon; and
   (e) a latching assembly mounted to the inner door so as to be adjacently disposed to the locking element when the inner door is covering the front opening, the latching assembly including:
      (i) a tongue configured to be received within the slot of the locking element; and
      (ii) a handle connected with the tongue such that rotation of the handle about a first axis facilitates rotation of the tongue, the handle being selectively movable between a first position and a second position, in the first position at least a portion of the handle is disposed over at least a portion of the locking element so that the handle functions as a spacing element that prevents complete closing of the outer door, in the second position the handle is spaced apart from the locking element such that the outer door is free to completely close.

2. An apparatus as recited in claim 1, wherein the inner door is transparent.

3. An apparatus as recited in claim 1, wherein the tongue is received within the slot of the locking element when the handle is moved from the first position to the second position.

4. An apparatus as recited in claim 1, wherein the slot of the locking element is at least partially bounded by a bearing surface, at least a portion of the bearing surface sloping toward the housing.

5. An apparatus as recited in claim 1, further comprising a sealing element mounted on the housing around at least a portion of the opening.

6. An apparatus as recited in claim 1, wherein the handle is rotatably connected to the hub about a second axis that is substantially perpendicular to the first axis.

7. An apparatus as recited in claim 6, wherein the handle with respect to the second axis is limited to rotating through an angle that is less than 90° relative to the plane of the inner door.

8. An apparatus as recited in claim 6, further comprising a spring mounted to the handle and biasing the handle away from the inner door.

9. An apparatus as recited in claim 1, wherein the handle is configured to be substantially disposed within the plane of the locking element when the handle is in the second position and the outer door is closed.

10. An incubator or drying oven comprising:
    (a) a housing bounding a useful space, the useful space communicating with the exterior through a front opening;
    (b) an inner door hingedly mounted to the housing and configured to selectively cover the front opening;
    (c) an outer door configured to at least partially cover the inner door;
    (d) a locking element located on the housing adjacent to the front opening, the locking element having a slot formed thereon; and
    (e) a latching assembly located on the inner door so as to be adjacently disposed to the locking element when the inner door is covering the opening, the latching assembly including:
       (i) a hub rotatably connected to the inner door about a first axis;
       (ii) a tongue radially outwardly projecting from the hub, the tongue being configured to be received within the slot of the locking element; and
       (iii) a handle connected with the tongue such that rotation of the handle about the first axis facilitates rotation of the tongue, the handle being selectively movable between a first position and a second position, in the first position at least a portion of the handle is disposed over at least a portion of the locking element so that the handle functions as a spacing element that prevents complete closing of the outer door, in the second position the handle is spaced apart from the locking element such that the outer door is free to completely close.

11. Apparatus as recited in claim 10, wherein the tongue is received within the slot of the locking element when the handle is moved from the first position to the second position.

12. Apparatus as recited in claim 10, wherein the slot of the locking element is at least partially bounded by a bearing surface, at least a portion of the bearing surface sloping toward the housing.

13. Apparatus as recited in claim 10, wherein the handle is rotatably connected to the hub about a second axis that is substantially perpendicular to the first axis.

14. Apparatus as recited in claim 13, wherein the handle with respect to the second axis is limited to rotating through an angle that is less than about 70° relative to the plane of the inner door.

15. Apparatus as recited in claim 13, further comprising a spring mounted to the handle and biasing the handle away from the inner door.

16. An incubator or drying oven comprising:
 (a) a housing bounding a useful space, the useful space communicating with the exterior through a front opening;
 (b) an inner door hingedly mounted to the housing and configured to selectively cover the front opening;
 (c) an outer door configured to at least partially cover the inner door;
 (d) a locking element located on the housing adjacent to the front opening, the locking element having a slot formed thereon; and
 (e) a latching assembly located on the inner door so as to be adjacently disposed to the locking element when the inner door is covering the opening, the latching assembly including:
  (i) a hub rotatably connected to the inner door about a first axis;
  (ii) a tongue radially outwardly projecting from the hub, the tongue being configured to be received within the slot of the locking element; and
  (iii) a handle rotatably connected to the hub about a second axis that is substantially perpendicular to the first axis, the handle being limited with respect to the second axis to rotating through an angle that is less than 90° relative to the plane of the inner door, the handle also be rotatable relative to the first axis between a first position wherein the tongue is disposed outside the slot of the locking element and a second position wherein the tongue is received within the slot of the locking element.

17. Apparatus as recited in claim 16, wherein at least a portion of the handle is disposed over at least a portion of the locking element so that the handle functions as a spacing element that prevents complete closing of the outer door when the handle is in the first position.

18. Apparatus as recited in claim 16, wherein the handle is spaced apart from the locking element such that the outer door is free to completely close when the handle is in the second position.

19. Apparatus as recited in claim 16, wherein the handle is limited with respect to the second axis to rotating through an angle that is less than 70° relative to the plane of the inner door.

20. Apparatus as recited in claim 16, further comprising a spring mounted to the handle and biasing the handle away from the inner door.

21. An incubator or drying oven comprising:
 (a) a housing bounding a useful space, the useful space communicating with the exterior through a front opening;
 (b) an inner door hingedly mounted to the housing and configured to selectively cover the front opening;
 (c) an outer door configured to at least partially selectively cover the inner door;
 (d) a locking element located on the housing; and
 (e) a handle rotatably mounted on the inner door, the handle being selectively movable between a first position and a second position, in the first position at least a portion of the handle being disposed over at least a portion of the locking element so that the handle functions as a spacing element that prevents complete closing of the outer door, in the second position the handle being disposed such that the outer door is free to completely close.

22. An apparatus as recited in claim 21, further comprising a locking assembly of which the handle is a portion thereof, the locking assembly mechanically engaging the locking element when the handle is in the second position.

23. An apparatus as recited in claim 21, further comprising:
 (a) the locking element having an opening formed thereon; and
 (b) a tongue mounted to the handle, the tongue being received within the opening of the locking element when the handle is in the second position.

* * * * *